United States Patent [19]

Sutcu et al.

[11] Patent Number: 5,695,462
[45] Date of Patent: Dec. 9, 1997

[54] GAS INSUFFLATION NEEDLE APPARATUS AND METHOD OF USE

[75] Inventors: Maz Sutcu, New Hartford; John Gentelia, Madison; Neil Quinn, South Ilion, all of N.Y.

[73] Assignee: Conmed Corporation, Utica, N.Y.

[21] Appl. No.: 587,272

[22] Filed: Jan. 18, 1996

[51] Int. Cl.⁶ ................................... A61M 5/32
[52] U.S. Cl. ................... 604/51; 604/26; 604/264
[58] Field of Search .................. 604/49, 51, 52, 604/53, 23, 24, 264, 272, 273, 274

[56] References Cited

U.S. PATENT DOCUMENTS

| | | |
|---|---|---|
| 4,869,717 | 9/1989 | Adair . |
| 5,290,276 | 3/1994 | Sewell, Jr. . |
| 5,398,671 | 3/1995 | Ortiz et al. . |
| 5,407,427 | 4/1995 | Zhu et al. . |
| 5,421,821 | 6/1995 | Janicki et al. . |

Primary Examiner—John D. Yasko
Attorney, Agent, or Firm—Larson & Taylor

[57] ABSTRACT

An insufflation needle apparatus which creates a pneumoperitoneum during the preparation of a patient for endoscopic surgical procedures is disclosed. The insufflation needle apparatus is characterized by a helical needle having a central helical passageway for gas therethrough. The helical needle is associated with a guide support member which maintains the helical needle in position for insertion into a patient while at the same time permitting free rotation of the helical needle about the central longitudinal axis of the support member independent of movement of the support member. In this manner, an upward traction force can be exerted on the support member to gently pull the wall of a patient's body cavity upwardly away from vulnerable internal organs while at the same time a downward force can be exerted on the helical needle while it is rotated in order to penetrate the peritoneum with the needle. The invention results in a safer method for gas insufflation and creation of a pneumoperitoneum during the preparation of patients for endoscopic surgical procedures.

20 Claims, 3 Drawing Sheets

GAS INSUFFLATION NEEDLE APPARATUS AND METHOD OF USE

FIELD OF THE INVENTION

The present invention relates to instruments for performing endoscopic procedures, and more particularly, to a gas insufflation needle apparatus for insufflating a body cavity prior to an endoscopic surgical procedure.

BACKGROUND OF THE INVENTION

Before performing an endoscopic surgical procedure, it is first necessary to insufflate a body cavity of the patient in order to separate the wall of the body cavity from the internal organs in the cavity. This separation creates room in which a surgical procedure may be performed using endoscopic instruments.

Insufflation is typically performed by insertion of a verres needle into the body cavity and subsequent injection of gas through the needle into the body cavity in order to inflate the body cavity and separate the wall of the body cavity from the internal organs housed therein. Subsequently, a trocar is inserted through the wall of the body cavity to provide a means which allows endoscopic instruments to be inserted into the body cavity without depressurizing the body cavity.

One example of a gas insufflation needle provided with an instrument port is shown in U.S. Pat. No. 4,869,717 (Adair). Another example of an insufflation needle with a viewing system is disclosed in U.S. Pat. No. 5,290,276 (Sewell, Jr.). U.S. Pat. No. 5,421,821 depicts a verres needle systems for use in the insufflation of a body cavity prior to performing endoscopic surgical procedures.

One problem with these known insufflation needles is that it remains difficult to determine with a high degree of precision the exact location of the tip of the verres needle in the body. It is necessary to position the tip of the needle at a location in the body cavity in order to achieve successful insufflation.

One method for determining the location of the tip of the needle is the saline injection/aspiration test. In this method a saline solution is injected through the verres needle into the body cavity and then the needle is aspirated. If the saline solution returns upon aspiration, this is an indication that the needle is improperly positioned.

Another problem with these insufflation needles is that the tip of the needle could end up in an organ, artery or the bowel in which case performing the insufflation technique would result in compressed gas being injected into the organ, artery or bowel with potential severe consequences for the patient. There is significant risk of this occurring when a straight verres needle is employed since sufficient downward force must be exerted on the wall of the body cavity to ensure full insertion of the verres needle. As a result, it is difficult to control the distance of penetration of the needle during insertion and thus internal organs, arteries and bowels are at risk.

Accordingly, in order to reduce the risk that the tip of the insufflation needle will penetrate an internal organ, artery or bowel, it is desirable to apply an upward traction force to the wall of the body cavity at the same time that the insufflation needle is inserted. In this manner, the wall of the body cavity can be pulled upwardly away from the internal organs, arteries, and bowel while the needle is being inserted in order to significantly reduce the risk that the tip of the needle will penetrate one of these internal organs.

An abdominal lift device for lifting the wall of a body cavity for insertion of endoscopic instruments is disclosed in U.S. Pat. No. 5,398,671. This lift device is inserted into the abdominal wall and is used to grip and raise the abdominal wall for subsequent insertion of endoscopic instruments. However, this device suffers from a number of problems such as the fact that it is cumbersome since a support structure is required to maintain the abdominal lift in position during the surgical procedure. Further, there is no provision for lifting the abdominal wall during insertion of the abdominal lift and, as a result, there is a risk to internal organs during insertion of the abdominal lift. Finally, this device cannot be used to insufflate a body cavity.

U.S. Pat. No. 5,407,427 (Zhu et al) discloses a trocar facilitator for endoscopic surgery. The embodiment shown in FIGS. 23-31 of this patent employs a corkscrew-like needle which may be provided with a passageway through which insufflation gas may be injected. The corkscrew-like needle is employed to penetrate the body cavity wall and peritoneum, to insufflate the body cavity and to anchor the trocar facilitator for subsequent insertion of endoscopic instruments through the facilitator and in the center of the corkscrew-like needle.

The apparatus of Zhu et al is provided with handles for the exertion of an upward traction force during the insertion of endoscopic instruments. However, this device suffers from the problem that during insertion of the corkscrew-like needle it is necessary to press down and rotate the entire trocar facilitator against the abdominal wall. As a result, this device does not reduce the risk of penetrating an internal organ, artery or bowel during insertion of the needle into the body cavity. This device does not contemplate exerting an upwardly directed traction force during insertion of the corkscrew-like needle.

Accordingly, it is the primary object of the present invention to provide an improved insufflation needle apparatus which permits the application of an upward traction force concurrently with the insertion of the insufflation needle into the body cavity of a patient.

It is a further object of the present invention to provide an insufflation needle apparatus which is simple to use and easy to manufacture.

These and other objects of the present invention will be apparent from the summary and detailed description which follow.

SUMMARY OF THE INVENTION

The present invention relates to an insufflation needle apparatus and method whereby an insufflation needle can be inserted into a body cavity with a reduced risk of contacting an internal organ, artery or bowel. The insufflation needle apparatus includes a helical needle for rotatably engaging tissue and penetrating the peritoneum of a patient. The helical needle has a proximal end, a distal end, and a helical passageway through the needle whereby gas may be administered through the needle into a patient. The insufflation needle apparatus also includes a guide support member having a bottom end, a top end, a central longitudinal axis, and an opening through the bottom end for passage of the helical needle. The guide support member is further characterized in that the top end of the guide support member is adapted for the application of an upwardly directed traction force to the guide support member. The guide support member also includes means for guiding and supporting the helical needle about the central longitudinal axis of the guide support member with the helical needle extending through the opening while permitting the helical needle to rotate about the central longitudinal axis of the guide support member independent of movement of the guide support member.

The apparatus provides the ability to insert the helical needle into the body cavity of a patient by rotating the needle about the central longitudinal axis of the guide support member while applying an upwardly directed traction force to the guide support member. In this manner the wall of the body cavity can be pulled upwardly away from the internal organs, arteries, or bowel while the insufflation needle is inserted. In this manner the risk of penetrating an internal organ, artery or bowel of the patient during insertion of the insufflation needle is substantially reduced.

To perform the method of the present invention, the insufflation needle apparatus of the invention is positioned with the bottom end of the guide support member in contact with the outside of the wall of a body cavity of a patient. The helical needle is supported on the guide support member for rotation about the central longitudinal axis of the guide support member with the proximal end of the need aligned with the opening in the bottom end of the guide support member. Subsequently, the helical needle is rotated about the central longitudinal axis of the guide support member such that the proximal end of the needle passes through the opening in the bottom end of the guide support member and penetrates and engages the wall of the body cavity of the patient. Once the body cavity wall is engaged, an upwardly directed traction force is applied to the top end of the guide support member to gently lift the wall of the body cavity away from the internal organs housed therein. Rotation of the helical needle is continued while maintaining the upward traction force until the proximal end of the helical needle penetrates the peritoneum. Finally, insufflation gas pressure is applied to the body cavity through the passageway in the helical needle to insufflate the body cavity and thereby create a pneumoperitoneum.

The method of the present invention significantly reduces the risk associated with insufflating the body cavity of a patient by gently lifting the wall of the body cavity away from vulnerable internal organs while inserting the insufflation needle into the patient. In this way, the likelihood that the insufflation needle will contact an internal organ, artery or bowel during insertion is substantially reduced.

DETAILED DESCRIPTION OF THE PREFERRED EMBODIMENTS

Figure 1:
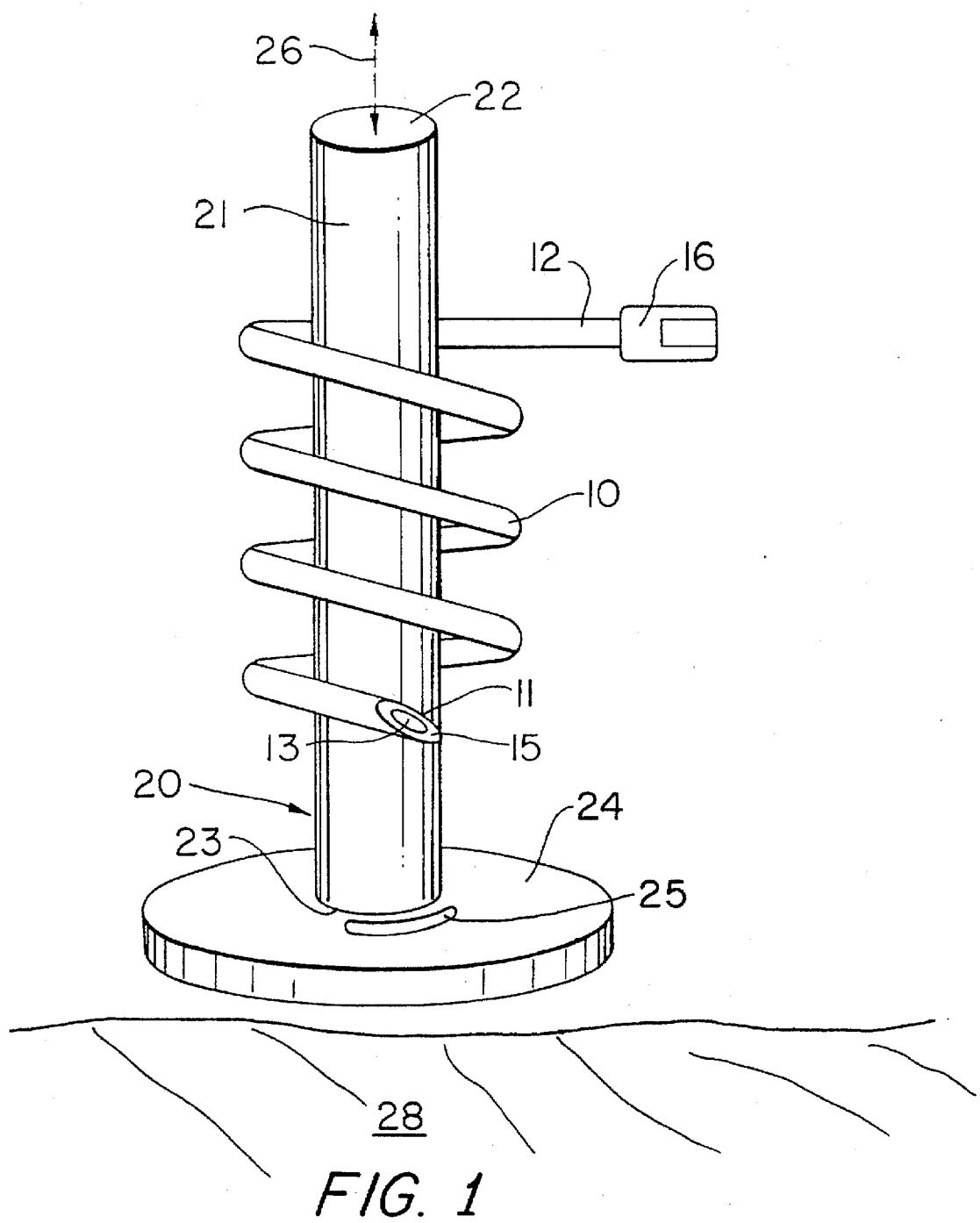
FIG. 1 is a side elevation of a first embodiment of the needle insufflation apparatus of the present invention with the needle is supported on the outside of the guide support member.

A first embodiment of the insufflation needle apparatus of the present invention is shown in FIG. 1. The insufflation needle apparatus includes a helical needle 10 and guide support member 20. Helical needle 10 has a proximal end 11 and a distal end 12 and is provided with a helical passageway 13 which passes through the entire length of helical needle 10 from the proximal end 11 to the distal end 12. The proximal end 11 of helical needle 10 is preferably provided with an inclined face 15. Attached to the distal end 12 of helical needle 10 is a luer lock 16 which permits fluid connection of helical passageway 13 to an apparatus for applying gas pressure.

Guide support member 20 is formed from a cylindrical member 21 which has a top end 22 and a bottom end 23. The bottom end 23 of cylindrical member 21 is provided with an outwardly extending flange 24 which has an arcuate slot 25 therein. The insufflation needle apparatus of FIG. 1 is shown positioned in the proper orientation relative to tissue 28 of the wall of a body cavity of a patient to begin the method of the present invention.

To employ the device of the invention, guide support member 20 is positioned in contact with tissue 28 in the orientation shown in FIG. 1 with bottom end 23 and outwardly extending flange 24 resting against tissue 28. Helical needle 10 is positioned around cylindrical member 21 as shown in FIG. 1 and the proximal end 11 of the helical needle 10 is then aligned with arcuate slot 25 in the first position ready for insertion into the tissue 28.

To insert helical needle 10 into tissue 28, helical needle 10 is rotated about the central longitudinal axis 26 in the direction of proximal end 11 while guide support member 20 remains stationary. Rotation of helical needle 10 causes the proximal end 11 of helical needle 10 to pass through arcuate slot 25 and into tissue 28 where it will penetrate and engage the wall of the body cavity of a patient. The penetration of helical needle 10 into tissue 28 occurs in essentially the same way that a cork-screw penetrates a cork.

Once helical needle 10 has penetrated sufficiently to provide a solid grip on tissue 28, an upward traction is applied to top end 22 of cylindrical member 21 to gently lift tissue 28 away from the internal organs, arteries, and bowel of the patient. Once tissue 28 is lifted, it is maintained in position by continuing application of upward traction on the top end 22 of cylindrical member 21 while helical needle 10 is rotated further until proximal end 11 of helical needle 10 penetrates the peritoneum of the patient and reaches the second position where it is ready for insufflation.

When it is believed that the peritoneum of the patient has been penetrated by the proximal end 11 of helical needle 10, it is good practice to confirm that the proximal end 11 of helical needle 10 is correctly positioned in the body cavity by using one of the well-known methods such as the saline injection/aspiration test. This test is performed by injecting saline solution via luer lock 16 and helical passageway 13 of helical needle 10 into the body cavity of the patient and subsequently aspirating the body cavity of the patient via luer lock 16 and helical passageway 13 of helical needle 10. If the proximal end 11 of helical needle 10 has, in fact, penetrated the peritoneum of the patient, it will be located in a large open space which will permit the injected saline solution to move away from proximal end 11 of helical needle 10. As a result, if aspiration of the body cavity does not result in the return of saline solution, this confirms that proximal end 11 of helical needle 10 has penetrated the peritoneum. If saline solution does return through helical passageway 13 of helical needle 10 repositioning of the proximal end 11 of helical needle 10 is indicated.

Outwardly extending flange 24 is preferably circumferential as shown in FIG. 1 since this increases the stability of the device as it rests against the patient during insertion of the helical needle 10. However, it is also possible to minimize the size of the flange 24 so that it is just large enough to accommodate the arcuate slot 25.

In a preferred embodiment of the apparatus depicted in FIG. 1, cylindrical member 21 has a diameter sufficient to ensure that helical needle 10 fits snugly over cylindrical member 21. A snug fit between helical needle 10 and cylindrical member 21 prevents helical needle 10 from moving laterally in order to minimize tissue damage.

Arcuate slot 25 is large enough to permit helical needle 10 to pass through outwardly extending flange 24 located at the bottom end 23 of cylindrical member 21. The arcuate shape of arcuate slot 25 conforms to the arc of helical needle 10. Arcuate slot 25 also provides a contact point between helical needle 10 and guide support member 20 since helical needle 10 will rest on outwardly extending flange 24 at one end of arcuate slot 25 at all times while the helical needle 10 passes through arcuate slot 25. As a result, when upward traction is exerted on top end 22 of cylindrical member 21, outwardly extending flange 24 will pull upwardly on helical needle 10 by virtue of the contact between helical needle 10 and outwardly extending flange 24 at the edge of arcuate slot 25.

Despite the fact that the upward traction force is transferred to the helical needle 10 in this manner, helical needle 10 is still able to freely rotate about the central longitudinal axis 26 during application of upward traction on cylindrical member 21. This is because the shape of helical needle 10 and arcuate slot 25 minimizes the contact area between helical needle 10 and outwardly extending flange 24. This allows helical needle 10 to slide along the edge of arcuate slot 25 as helical needle 10 is rotated while at the same time maintaining the contact between helical needle 10 and outwardly extending flange 24 in order to continue to transmitting the upward traction from cylindrical member 21 to helical needle 10 and tissue 28. Slippage of helical needle 10 along arcuate slot 25 due to application of upward traction on cylindrical member 21 is prevented by outwardly extending flange 24 which pins tissue 28 between itself and helical needle 10.

Figure 2:
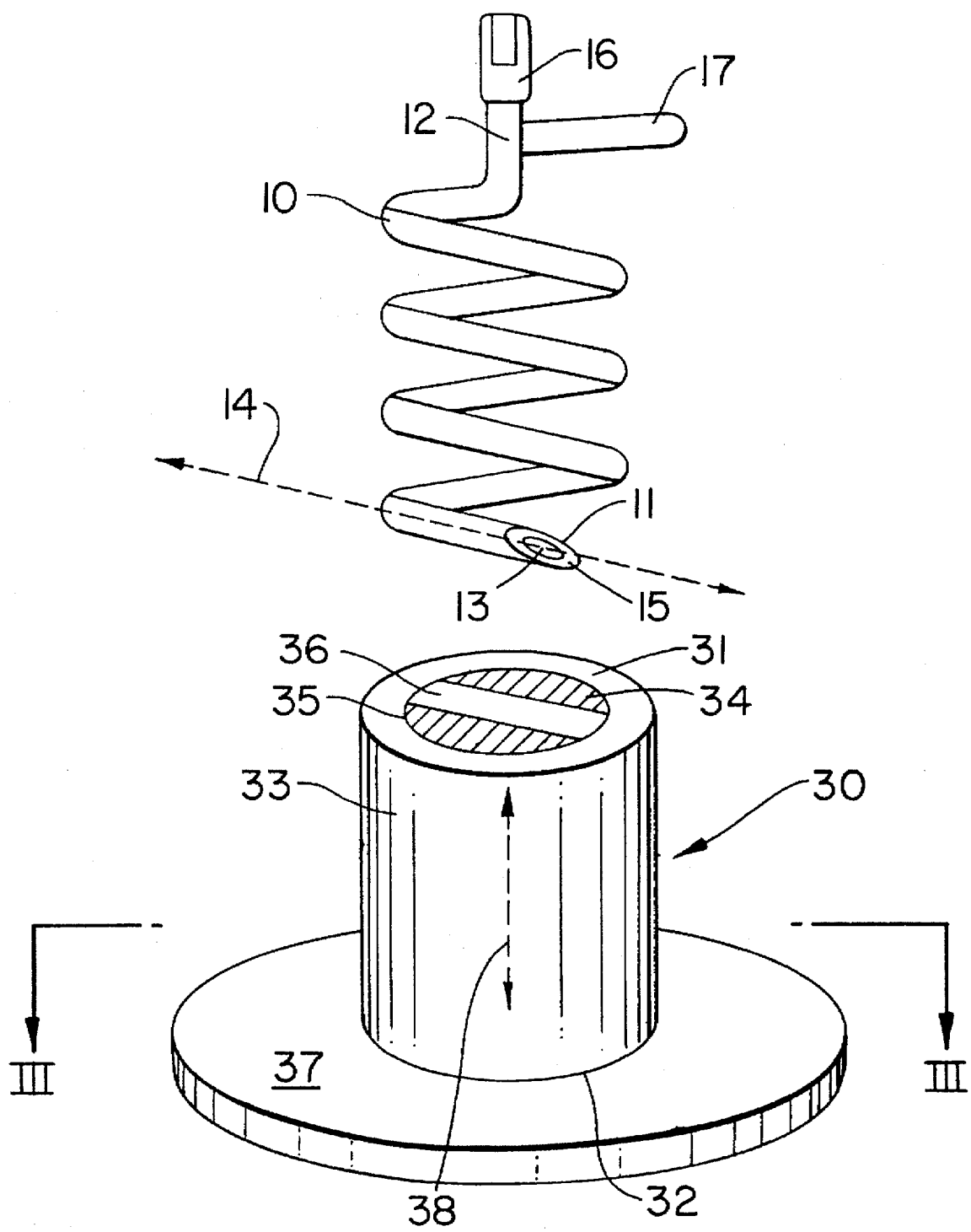
FIG. 2 is an exploded side elevation of a second embodiment of the present invention employing a hollow guide support member.

Referring now to FIG. 2, there is shown a second, more preferred embodiment of the present invention with helical needle 10 depicted separately from guide support member 30. In this alternative embodiment, helical needle 10 is preferably provided with a handle 17 in addition to the features described above with respect to FIG. 1. In addition, distal end 12 of helical needle 10 is angled upwardly in this embodiment to provide access to luer lock 16 when helical needle 10 is in the second position fully extended downwardly from guide support member 30.

Details of the proximal end 11 of helical needle 10 are also shown in FIG. 2. More particularly, inclined face 15 of the proximal end 11 of helical needle 10 is, in a preferred embodiment, angled with respect to the central axis 14 of helical passageway 13 in order to reduce or prevent tissue coring during insertion of helical needle 10 into the body. In a preferred embodiment, inclined face 15 is ground at an inclination to central axis 14 of helical passageway 13 of 10° to 15° whereby tissue coring during needle insertion is substantially prevented.

In another preferred embodiment of helical needle 10 the plane of inclined face 15 is tilted with respect to the central longitudinal axis 38 of guide support member 30 so that upon rotation of helical needle 10 the proximal end 11 of helical needle 10 tends to drive deeper into tissue 28 rather than deflect upwards or sideways by contact with tissue 28. These two features of proximal end 11 of helical needle 10 both tend to further reduce tissue damage during insertion of helical needle 10.

Also shown in FIG. 2 is an alternative embodiment of guide support member 30. In this embodiment, guide support member 30 includes a top end 31, a bottom end 32 and a hollow cylindrical member 33. Hollow cylindrical member 33 has an inner wall 34 which forms a cylindrical bore 35 that is adapted to receive helical needle 10. In a preferred embodiment, inner wall 34 of hollow cylindrical member 33 defines a helical track 36 which is adapted to receive, support and guide helical needle 10 through its full range of rotation from the first position to the second position.

The embodiment of FIG. 2 may also include an outwardly extending flange 37 affixed to bottom end 32 of guide support member 30 although this is not necessary. The flange 37 improves stability as set forth above. Hollow cylindrical member 33 is adapted to receive, guide and support helical needle 10 about central longitudinal axis 38 of hollow cylindrical member 33 while permitting helical needle 10 to freely rotate about central longitudinal axis 38 of hollow cylindrical member 33 from a first position wherein proximal end 11 of helical needle 10 is aligned with arcuate slot 39 (shown in FIG. 3) to a second position where proximal end 11 of helical needle 10 is fully extended downwardly from guide support member 30 to penetrate the peritoneum of a patient.

Figure 3:
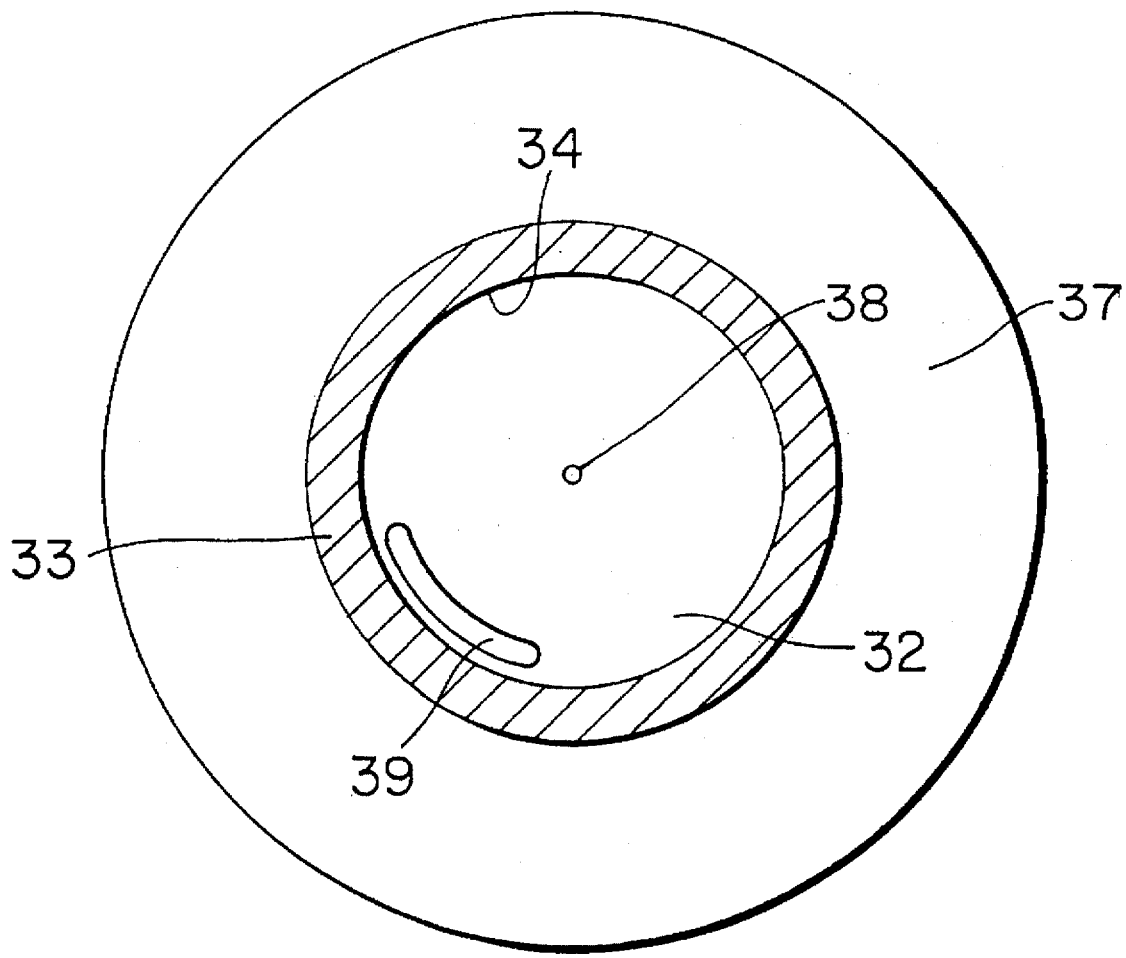
FIG. 3 is a cross-sectional view of the embodiment of FIG. 2 taken along the line III—III.

Referring now to FIG. 3, there is shown a cross-sectional view along line III—III of FIG. 2. This cross-sectional view shows the position of arcuate slot 39 within the confines of inner wall 34 of hollow cylindrical member 33 and penetrating bottom end 32 of guide support member 30.

The operation of the apparatus shown in FIGS. 2–3 is much the same as the operation of the apparatus shown in FIG. 1 with the exception that helical needle 10 is supported and guided within cylindrical bore 35 of hollow cylindrical member 33. In this embodiment, the distal end 12 of helical needle 10 protrudes from the top end 31 of hollow cylindrical member 33. This allows access to luer lock 16 of helical needle 10. Handle 17 of helical needle 10 is also accessible since it remains above the top end 31 of hollow cylindrical member 33 through the full range of motion of helical needle 10. Thus, rotation of helical needle 10 can be accomplished by grasping handle 17 while, at the same time, applying an upward traction to the top end 31 of hollow cylindrical member 33.

Inner wall 34 may include a helical track 36. In this case, helical needle 10 is inserted into helical track 36 when it is positioned in cylindrical bore 35. Helical track 36 helps guide the needle into the arcuate slot 39, stabilizes the helical needle 10 in the cylindrical bore 35 and reduces the chance of accidentally dropping helical needle 10 while handling the insufflation needle apparatus. Proximal end 11 of helical needle 10 is aligned with arcuate slot 39 and the bottom end 32 and outwardly extending flange 37 of hollow cylindrical member 33 are placed in contact with the wall of a body cavity of a patient.

Then, helical needle 10 is rotated within cylindrical bore 35 such that the proximal end 11 of helical needle 10 passes through arcuate slot 39 and engages and penetrates the wall of the body cavity. Once helical needle 10 has penetrated the wall of the body cavity sufficiently to provide a firm grip, an upward traction force is exerted on hollow cylindrical member 33 to gently lift the wall of the body cavity away from the internal organs, arteries and bowels of the patient. Subsequently, while continuing to apply upward traction on hollow cylindrical member 33, helical needle 10 is further rotated to cause the proximal end 11 of helical needle 10 penetrates the peritoneum of the patient.

At that point, the saline injection/aspiration test may be employed to confirm the position of the proximal end 11 of helical needle 10. Once the position of the proximal end 11 of helical needle 10 is confirmed, a source of gas pressure (not shown) is connected to luer lock 16 of helical needle 10. Finally, gas pressure is applied to the body cavity of the patient via luer lock 16 and helical passageway 13 of helical needle 10 in order to create a pneumoperitoneum. Thereafter, endoscopic surgical procedures can be carried out in the usual manner.

In the embodiment shown in FIGS. 2–3, it is desirable that helical needle 10 fit snugly within hollow cylindrical member 33 of guide support member 30. In order to accomplish this, cylindrical bore 35 is made just large enough to receive helical needle 10 snugly therein. In the embodiment employing helical track 36, helical track 36 is proportioned for a snug fit with helical needle 10 in order to prevent lateral movement of helical needle 10 while at the same time permitting rotational movement about central longitudinal axis 38 of hollow cylindrical member 33.

The following example of the invention is presented for the purpose of illustration and description only and is not to be construed as limiting the invention in any way. The scope of the invention is to be determined from the claims appended hereto.

EXAMPLE

An insufflation needle apparatus of the type depicted in FIG. 1 was fabricated by machining the guide support member 20 from Delrin™ and ultra-high molecular weight polyethylene polymer. For mass production, the guide support member may be injection molded.

Helical needle 10 was made using 16-gauge type 304 hypodermic tubing. The outer diameter of the hypodermic tubing is 0.065 inches, the inner diameter is 0.047 inches and the hypodermic tubing has a nominal wall thickness of 0.009 inches. The hypodermic tubing was coiled. The coil had an inner diameter of 0.676 inches and was coiled with two coils per inch.

The proximal end 11 of helical needle 10 was ground at an angle of about 13° to the central axis 14 of helical passageway 13. The grinding plane was tilted with respect to the central longitudinal axis of the coil in order to provide a proximal end 11 of helical needle 10 which tends to drive deeper into the tissue rather than deflect sideways upon rotation of helical needle 10.

This prototype was tested in animal surgery experiments and, as expected, the insufflation needle apparatus allowed the operator to gently pull the abdominal wall upwards while at the same time driving the needle downward through the abdominal wall with a rotational motion. In this manner, a safer insertion of the needle was accomplished since the abdominal wall was retracted away from vulnerable internal organs during insertion of the needle.

What is claimed is:

1. An insufflation needle apparatus comprising:
    a helical needle for rotatably engaging tissue and penetrating the peritoneum of a patient, said needle having a proximal end, a distal end, and a helical passageway through said needle for administration of gas through the needle into a patient; and
    a guide support member having a bottom end, a top end, a central longitudinal axis, an opening through the bottom end for passage of the helical needle, and wherein the top end of the guide support member is adapted for the application of an upwardly directed traction force to the guide support member; and
    said guide support member including means for guiding and supporting said helical needle about the central longitudinal axis of the guide support member with the helical needle extending through said opening, while permitting said helical needle to rotate about the central longitudinal axis of the guide support member independent of movement of the guide support member.

2. An insufflation needle apparatus as claimed in claim 1 wherein said helical needle is capable of rotation about the central longitudinal axis of said guide support member from a first position wherein the proximal end of said needle is positioned for tissue engagement, to a second position wherein the proximal end of said needle is downwardly extended from said guide support member a sufficient distance to penetrate the peritoneum of the patient.

3. An insufflation needle apparatus as claimed in claim 2 wherein the opening in the proximal end of the guide support member is an arcuate slot.

4. An insufflation needle apparatus as claimed in claim 3 wherein said passageway has a central axis and the proximal end of said helical needle forms an inclined face which is angled relative to the central axis of the passageway to reduce coring of said tissue during needle rotation.

5. An insufflation needle apparatus as claimed in claim 4 wherein the inclined face of said needle is angled 10–15 degrees relative to the central axis of the passageway.

6. An insufflation needle apparatus as claimed in claim 4 wherein the inclined face of said helical needle is inclined relative to the central axis of the guide support member to reduce deflection of said helical needle by the tissue during needle rotation.

7. An insufflation needle apparatus as claimed in claim 3 wherein the means for guiding and supporting includes a cylindrical member which extends upwardly from the bottom end of the guide support member by a length sufficient to extend beyond the distal end of said helical needle when said needle is in the first position, said cylindrical member having a diameter sufficient to ensure that said helical needle fits snugly over said cylindrical member.

8. An insufflation needle apparatus as claimed in claim 7 wherein said arcuate slot is located in said outwardly extending flange adjacent to the cylindrical member.

9. An insufflation needle apparatus as claimed in claim 8 further comprising a luer lock affixed to the distal end of the helical needle.

10. An insufflation needle apparatus as claimed in claim 2 wherein the means for guiding and supporting includes an upwardly extending, hollow cylindrical member which has an inner wall that defines a cylindrical bore having an inside diameter large enough to receive said helical needle.

11. An insufflation needle apparatus as claimed in claim 10 wherein the helical needle is of sufficient length that the distal end of the helical needle extends beyond the top end of said hollow cylindrical member when the helical needle is in said second position.

12. An insufflation needle apparatus as claimed in claim 11 wherein the arcuate slot is located in the bottom end of the guide support member within the cylindrical bore of said hollow cylindrical member.

13. An insufflation needle apparatus as claimed in claim 12 further comprising a handle attached at or near the distal end of the helical needle.

14. An insufflation needle apparatus as claimed in claim 12 wherein said means for guiding and supporting further includes a helical track located in the inner wall of the hollow cylindrical member and which is adapted to receive said helical needle and to guide said helical needle through its full range of rotational movement from said first position to said second position.

15. An insufflation needle apparatus as claimed in claim 12 further comprising a luer lock affixed to the distal end of the helical needle.

16. An insufflation needle apparatus as claimed in claim 3 further comprising an outwardly extending flange attached to the bottom end of the guide support member.

17. An insufflation needle apparatus as claimed in claim 16 wherein the arcuate slot is located in the outwardly extending flange.

18. A method for the insufflation of a body cavity of a patient by penetration of the peritoneum with an insufflation needle and creation of a pneumoperitoneum, said method comprising the steps of:

positioning an insufflation needle apparatus as claimed in claim 1 with the bottom end in contact with the wall of a body cavity a patient, and with the helical needle supported for rotation about the central longitudinal axis of said guide support member, rotating the helical needle about the central longitudinal axis of the guide support member such that the proximal end of the needle passes through the opening in the bottom end of the guide support member and penetrates and engages the wall of the body cavity of the patient, applying sufficient upward traction on the top end of the guide support member to gently lift the wall of the body cavity, continuing rotation of the helical needle while applying the upward traction until the proximal end of the helical needle penetrates the peritoneum, and applying insufflation gas pressure to the body cavity through the passageway in the helical needle to create the pneumoperitoneum.

19. A method as claimed in claim 18 further comprising the step of determining if the helical needle has penetrated the peritoneum prior to the step of applying the insufflation gas pressure.

20. A method as claimed in claim 19 wherein said determining step comprises the steps of injecting a saline solution into the patient through the passageway in the helical needle, aspirating the patient through the passageway in the helical needle, and checking the material obtained from aspirating the passageway of the helical needle for saline solution to determine if the peritoneum has been penetrated by the helical needle.

* * * * *

UNITED STATES PATENT AND TRADEMARK OFFICE
Certificate

Patent No. 5,695,462                                                      Patented: December 9, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Maz Sutco, John S. Gentelia, Neil Quinn and Pasquale Ciaglia.

Signed and Sealed this Ninteenth Day of May, 1998.

<div style="text-align: right;">
WYNN WOOD COGGINS<br>
*Supervisory Patent Examiner*<br>
Art Unit 3306
</div>